US009250064B2

(12) United States Patent
Pfaff

(10) Patent No.: US 9,250,064 B2
(45) Date of Patent: *Feb. 2, 2016

(54) MULTIPLE BEAM TRANSMISSION INTERFEROMETRIC TESTING METHODS FOR THE DEVELOPMENT AND EVALUATION OF SUBWAVELENGTH SIZED FEATURES WITHIN SEMICONDUCTOR AND ANISOTROPIC DEVICES

(71) Applicant: Attofemto, Inc., Lake Oswego, OR (US)

(72) Inventor: Paul L. Pfaff, Lake Oswego, OR (US)

(73) Assignee: Attofemto, Inc., Lake Oswego, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/522,334

(22) Filed: Oct. 23, 2014

(65) Prior Publication Data

US 2015/0041657 A1 Feb. 12, 2015

Related U.S. Application Data

(63) Continuation of application No. 13/903,232, filed on May 25, 2013, now Pat. No. 8,879,071, which is a continuation of application No. 13/366,180, filed on Feb. 3, 2012, now Pat. No. 8,462,350, which is a (Continued)

(51) Int. Cl.
*G01B 11/02* (2006.01)
*G01B 11/16* (2006.01)

(Continued)

(52) U.S. Cl.
CPC .......... *G01B 11/164* (2013.01); *G01B 11/2441* (2013.01); *G01N 21/1717* (2013.01);

(Continued)

(58) Field of Classification Search
CPC .... G01B 9/021; G01B 9/023; G01B 11/2441; G01N 21/1717; G01N 21/23; G01N 2021/1721; H01L 22/12
See application file for complete search history.

(56) References Cited

U.S. PATENT DOCUMENTS 3,663,194 A 5/1972 Greenstein et al.
3,956,698 A 5/1976 Malmberg et al.

(Continued)

FOREIGN PATENT DOCUMENTS

WO 9729362 8/1997

OTHER PUBLICATIONS

Kristal, Richard, Pulsed HF Laser Holographic Interferometry, Applied Optics, vol. 14, No. 3, Mar. 1975.

(Continued)

*Primary Examiner* — Michael A Lyons
(74) *Attorney, Agent, or Firm* — George C. Rondeau, Jr.; Davis Wright Tremaine LLP

(57) ABSTRACT

Improved methods and systems for inspection imaging for holographic or interferometric semiconductor test and evaluation through all phases of device development and manufacture. Specifically, systems and methods are disclosed for extending the range of optical holographic interferometric inspection for testing and evaluating microelectronic devices and determining the interplay of electromagnetic signals and dynamic stresses to the semiconductor material are provided in which an enhanced imaging method provides continuous and varying the magnification of the optical holographic interferometric images over a plurality of interleaved optical pathways and imaging devices. Analysis of one or more holographic interference patterns displays internal and external stresses and the various effects of such stresses upon the operating characteristics of features within the features, interior structures or within the internal surfaces of the semiconductor device at any stage of development or manufacture.

20 Claims, 4 Drawing Sheets

Related U.S. Application Data continuation of application No. 12/779,749, filed on May 13, 2010, now Pat. No. 8,139,228, which is a continuation of application No. 12/120,924, filed on May 15, 2008, now Pat. No. 7,733,499, which is a continuation of application No. 11/278,389, filed on Mar. 31, 2006, now Pat. No. 7,400,411, which is a continuation of application No. 10/301,030, filed on Nov. 20, 2002, now Pat. No. 7,206,078.

(60) Provisional application No. 60/337,419, filed on Dec. 6, 2001.

(51) Int. Cl.
    *G01B 11/24*     (2006.01)
    *G01N 21/17*     (2006.01)
    *G01N 21/23*     (2006.01)
    *H01L 21/66*     (2006.01)
    *G01N 21/95*     (2006.01)

(52) U.S. Cl.
    CPC ............ *G01N21/23* (2013.01); *G01N 21/9501* (2013.01); *H01L 22/12* (2013.01); *G01N 2021/1721* (2013.01)

(56) References Cited

U.S. PATENT DOCUMENTS

| | | | |
|---|---|---|---|
| 4,053,833 | A | 10/1977 | Malmberg et al. |
| 4,188,123 | A | 2/1980 | Kleinknecht |
| 4,211,488 | A | 7/1980 | Kleinknecht |
| 4,242,635 | A | 12/1980 | Burns |
| 4,355,278 | A | 10/1982 | Burns et al. |
| 4,415,851 | A | 11/1983 | Langner et al. |
| 4,482,863 | A | 11/1984 | Auston et al. |
| 4,554,453 | A | 11/1985 | Feigt et al. |
| 4,618,819 | A | 10/1986 | Mourou et al. |
| 4,681,449 | A | 7/1987 | Bloom et al. |
| 4,703,260 | A | 10/1987 | Beha et al. |
| 4,714,826 | A | 12/1987 | Goutzoulis |
| 4,745,361 | A | 5/1988 | Nees et al. |
| 4,758,092 | A | 7/1988 | Heinrich et al. |
| 4,760,249 | A | 7/1988 | Baskett |
| 4,786,864 | A | 11/1988 | Beha et al. |
| 4,816,755 | A | 3/1989 | Look et al. |
| 4,827,212 | A | 5/1989 | Kamieniecki |
| 4,843,329 | A | 6/1989 | Beha et al. |
| 4,868,492 | A | 9/1989 | Beha et al. |
| 4,875,006 | A | 10/1989 | Henley et al. |
| 4,881,029 | A | 11/1989 | Kawamura |
| 4,896,109 | A | 1/1990 | Rauscher |
| 4,933,634 | A | 6/1990 | Cuzin et al. |
| 4,953,983 | A | 9/1990 | Bottka |
| 4,970,461 | A | 11/1990 | LePage |
| 4,983,911 | A | 1/1991 | Henley |
| 4,993,634 | A | 2/1991 | Hach et al. |
| 4,999,577 | A | 3/1991 | Beha et al. |
| 5,034,683 | A | 7/1991 | Takahaski et al. |
| 5,059,897 | A | 10/1991 | Aton et al. |
| 5,216,359 | A | 6/1993 | Makki et al. |
| 5,407,850 | A | 4/1995 | Doyle et al. |
| 5,422,723 | A | 6/1995 | Paranjpe et al. |
| 5,438,439 | A | 8/1995 | Mok et al. |
| 5,570,011 | A | 10/1996 | Henley |
| 5,682,236 | A | 10/1997 | Trolinger et al. |
| 5,895,972 | A | 4/1999 | Paniccia |
| 5,930,588 | A | 7/1999 | Paniccia |
| 5,969,517 | A | 10/1999 | Rao |
| 5,995,223 | A | 11/1999 | Power |
| 5,999,152 | A | 12/1999 | Liao et al. |
| 6,075,908 | A | 6/2000 | Paniccia et al. |
| 6,084,396 | A | 7/2000 | Rao |
| 6,163,378 | A | 12/2000 | Khoury |
| 6,166,846 | A | 12/2000 | Maloney |
| 6,172,752 | B1 | 1/2001 | Haruna et al. |
| 6,218,194 | B1 | 4/2001 | Lyndin et al. |
| 6,218,655 | B1 | 4/2001 | Ogasawara et al. |
| 6,231,194 | B1 | 5/2001 | Raj et al. |
| 6,246,098 | B1 | 6/2001 | Paniccia |
| 6,251,706 | B1 | 6/2001 | Paniccia |
| 6,269,199 | B1 | 7/2001 | Maloney |
| 6,323,985 | B1 | 11/2001 | Maloney |
| 6,374,003 | B1 | 4/2002 | Ding et al. |
| 6,421,473 | B1 | 7/2002 | Paniccia et al. |
| 6,434,289 | B1 | 8/2002 | Paniccia et al. |
| 6,449,405 | B1 | 9/2002 | Paniccia et al. |
| 6,458,495 | B1 | 10/2002 | Tsai et al. |
| 6,463,193 | B2 | 10/2002 | Paniccia et al. |
| 6,470,104 | B2 | 10/2002 | Paniccia et al. |
| 6,480,641 | B1 | 11/2002 | Ding et al. |
| 6,483,954 | B2 | 11/2002 | Koehl et al. |
| 6,501,092 | B1 | 12/2002 | NiKonor et al. |
| 6,512,385 | B1 | 1/2003 | Pfaff et al. |
| 6,522,812 | B1 | 2/2003 | NiKonor |
| 6,548,417 | B2 | 4/2003 | Dao et al. |
| 6,566,679 | B2 | 5/2003 | NiKonor et al. |
| 6,600,760 | B1 | 7/2003 | Green et al. |
| 6,600,864 | B2 | 7/2003 | Samara-Rubio et al. |
| 6,631,146 | B2 | 10/2003 | Pontis et al. |
| 6,642,531 | B1 | 11/2003 | Powers |
| 6,650,802 | B1 | 11/2003 | Morse et al. |
| 6,653,161 | B1 | 11/2003 | Morse |
| 6,658,031 | B2 | 12/2003 | Tuganov et al. |
| 6,660,649 | B2 | 12/2003 | Dao et al. |
| 6,665,321 | B1 | 12/2003 | Sochava et al. |
| 6,687,269 | B1 | 2/2004 | Rice et al. |
| 6,704,332 | B2 | 3/2004 | Chapman et al. |
| 6,724,790 | B1 | 4/2004 | Daiber et al. |
| 6,751,002 | B2 | 6/2004 | Ovadia et al. |
| 6,763,047 | B2 | 7/2004 | Daiber et al. |
| 6,778,102 | B1 | 8/2004 | Grunnet-Jepson et al. |
| 6,778,750 | B2 | 8/2004 | Vodrahalli et al. |
| 6,782,164 | B1 | 8/2004 | Lee et al. |
| 6,785,430 | B2 | 8/2004 | Paniccia |
| 6,788,724 | B2 | 9/2004 | Sell et al. |
| 6,788,727 | B2 | 9/2004 | Liu |
| 6,803,777 | B2 | 10/2004 | Pfaff et al. |
| 6,804,278 | B2 | 10/2004 | Daiber |
| 6,816,516 | B2 | 11/2004 | Daiber |
| 6,822,979 | B2 | 11/2004 | Daiber |
| 6,972,577 | B2 | 12/2005 | Pfaff et al. |
| 7,206,078 | B2 * | 4/2007 | Pfaff et al. ..................... 356/517 |
| 7,323,889 | B2 | 1/2008 | Pfaff et al. |
| 7,400,411 | B2 * | 7/2008 | Pfaff ............................. 356/503 |
| 7,420,687 | B2 | 9/2008 | Pfaff |
| 7,728,958 | B2 | 6/2010 | Pfaff |
| 7,733,499 | B2 * | 6/2010 | Pfaff ............................. 356/503 |
| 7,773,230 | B2 | 8/2010 | Pfaff |
| 8,139,228 | B2 * | 3/2012 | Pfaff ............................. 356/503 |
| 8,462,350 | B2 * | 6/2013 | Pfaff ............................. 356/503 |
| 8,879,071 | B2 * | 11/2014 | Pfaff ............................. 356/503 |
| 2003/0067312 | A1 | 4/2003 | Pfaff et al. |
| 2005/0036151 | A1 | 2/2005 | Gornick et al. |
| 2007/0018662 | A1 | 1/2007 | Pfaff |
| 2009/0147334 | A1 | 6/2009 | Chen et al. |

OTHER PUBLICATIONS

Weingarten, Kurt J., Picosecond Optical Sampling of GaAs Integrated Circuits, IEEE Journal of Quantum Electronics, vol. 24, No. 2, Feb. 1988.

Ek, L. et al., Detection of the Nodal Lines and the Amplitude of Vibration by Speckle Interferometry, Optics Communications, vol. 2, No. 9, Feb. 1971.

Lohmann and Paris, Computer Generated Spatial Filters for Coherent Optical Data Processing, Applied Optics, vol. 7, No. 4, Apr. 1968.

Lohmann A.W., Reconstruction of Vectorial Wavefronts, Applied Optics, vol. 4, No. 12, 1965.

Mandelis, Andreas, Laser Infrared Photothermal Radiometry of Semiconductors: Principles and Applications to Solid State Electronics, Solid-State Electronics, vol. 42, No. 1, 1998.

Mendlovic et al., Compact Optical Temporal Processors, Applied Optics, vol. 34, No. 20, Jul. 10, 1995.

(56) References Cited

OTHER PUBLICATIONS

Nakadate and Saito, Fringe Scanning Speckle-Pattern Interferometry, Applied Optics, vol. 24, No. 14, Jul. 1985.
Nassenstein, H., Superresolution by Diffraction of Subwaves, Optics Communications, vol. 2, No. 5, Oct. 1970.
Nikolova et al., Polarization-Preserving Wavefront Reversal by Four-Wave Mixing in Photoanisotropic Materials, Applied Optics, vol. 27, No. 8, Apr. 15, 1988.
O'Regan, R. et al., A New Holographic Interferometer for Stress Analysis, Experimental Mechanics, Jun. 1971.
P. Hariharan, "Optical Holigraphy: Principles, Techniques, and Application", 2nd ed. Cambridge University Press, 1996.
Paritskii, L.G. et al., Use of Semiconductors in Long-Wavelength Photography, Soviet Physics—Semiconductors, vol. 4, No. 4, Oct. 1970.
Paritskii et al., Formation of Photographic Images at the Interface Between a Semiconductor and an Active Gas Medium, Soviet Physics-Semiconductors, vol. 6, No. 7, Jan. 1973.
Rastogi and Pflug, Holographic Moire Phase Reinforcement Procedure to Obtain Variable Sensitivity Surface Topographic Mapping: Extension to Phase Stepping, 1992.
Rastogi and Pflug, Novel Concept for Obtaining Continuously Variable Topographic Contour Mapping Using Holographic Interferometry, Applied Optics, vol. 29, No. 29, Oct. 1990.
Rioux et al., Plastic Recording Media for Holography at 10.6 um, Applied Optics, vol. 16, No. 7, Jul. 1977.
Roberds, Donald W., Particle Sizing Using Laser Interferometry, Applied Optics, vol. 16, No. 7, Jul. 1977.
Saito et al., Enhancement of a Sensitivity by Stratifying a Photoconductor on Thermoplastic-Photoconductor Media, Journal of Optics, vol. 12, No. 1, 1981.
Saito et al., Solvent Vapour Method in Thermoplastic Photoconductor Media, Journal of Optics, vol. 11, No. 5, 1980.
Schmidt-Tiedmann, K.J., Experimental Evidence of Birefringence by Free Carriers in Semiconductors, Physical Review Letters, vol. 7, No. 10, Nov. 1961.
Schwider et al., Homogeneity Testing by Phase Sampling Interferometry, Applied Optics, vol. 24, No. 18, Sep. 15, 1985.
Snow and Vandewarker, An Application of Holography to Interference Microscopy, Applied Optics, vol. 7, No. 3, Mar. 1968.
Som and Budhiraja, Noise Reduction by Continuous Addition of Subchannel Holograms, Applied Optics, vol. 14, No. 7, Jul. 1975.
Soviet Physics—Semiconductors (excerpts), Feb. 4, 1981.
Srinath and Sarma, Role of Light Ellipse in Photoelasticity and New Methods for Isoclinic-parameter Determination, Experimental Mechanics, Jun. 1971.
Nakashima, Takashi et al., Optical Time Domain Reflectometer with a Laser Diode Operating as Light Emitter/Photodetector, Japanese Journal of Applied Physics, vol. 24, No. 2, Feb. 1985, pp. L135-L136.
Tilford, Charles R., Analytical Procedure for Determining Lengths from Fractional Fringes, Applied Optics, vol. 16, No. 7, Jul. 1977.
Todorov et al., Polarization Holography, Applied Optics, Mar. 1985.
Tull et al., Self-Scanned Digicon: a Digital Image Tube for Astronomical Spectroscopy, Applied Optics, vol. 14, No. 5, May 1975.
Vanin, V.A., Influence of the Polarization of the Object and Reference Waves on the Hologram Quality, Soviet Journal of Quantum Electron, vol. 9, No. 6, Jun. 1979.
Vienot et al., Three Dimensional Object Recognition in Real Time by Multiplex Spatial Filtering, Optics Communications, vol. 2, No. 9, Feb. 1971.
Woerdman "Formation of a Transient Free Carrier Hologram in Si" Optics Communications, Oct. 1970.
Yamaguchi and Takahashi, Ellipsometric Method for Separate Measurements of n and d of a Transparent Film, Applied Optics, vol. 14, No. 8, Aug. 1975.
Yatagai, Toyohiko, Cellular Logic Architectures for Optical Computers, Applied Optics, vol. 25, No. 10, May 15, 1986.
Yu et al., Direct Measurement of the Refractive Index Change of Silicon with Optically Injected Carriers, Applied Physics Letters, vol. 68, No. 11, Mar. 1996.

Zaidel et al., Plasma Diagnostics by Holography, Soviet Physics-Technical Physics, vol. 13, No. 9, Mar. 1969.
Zh. D.N. Goryachev et al., Photographic Process Based on Photoelectric Action of a Surface-Barrier Junction in Silicon, Soviet Physics—Semiconductors, Feb. 1971, vol. 4, No. 8, Leningrad, USSR.
Zhu, Wen-Hau, Holographic Tomography in Three-Dimensional Photoelasticity Within the Born Approximation, Journal of the Optics Society of America, vol. 9, No. 11, Nov. 1992.
Amadesi et al., Holgraphic Methods for Painting Diagnostics, Applied Optics, vol. 13, No. 9, Sep. 1974.
Applied Physics Letter (excerpts) Jan. 1969.
Asundi and Yung, Phase-Shifting and Logical Moire, Journal of the Optical Society of America, vol. 8, No. 10, Oct. 1991.
Thompson, B.J., Holographic Particle Sizing Techniques, Journal Physics E: Scientific Instruments, vol. 7, pp. 781-788, 1974.
Banyasz et al., Holography and Holographic Interferometry with a near IR Sensitive Photopolymer System, Journal De Physique III, No. 1, Jan. 1997.
Belyakov et al., Use of Evaporated Lead Sulfide Films in Electrolytic Photography, Soviet Physics—Semiconductors, vol. 5, No. 7, Jan. 1972.
Brandt, G.B., Hologram-Moire Interferometry for Transparent Objects, Applied Optics, vol. 6, No. 9, Sep. 1967.
Buse et al., Infrared Holographic Recording in $LiNbO_3$:Cu, Applied Physics, 1994.
Kurtz, C.N., Holographic Polarization Recording with an Encoded Reference Beam, Applied Physics Letters, vol. 14, No. 2, Jan. 1969.
Caulfield, H.J., A New Approach to Computer Holography, Optics Communications, vol. 2, No. 5, Oct. 1970.
Colburn et al., Holographic Recording in Thermoplastic at 1.15 um, Applied Physics Letters, vol. 23, No. 3, Aug. 1973.
Courjon et al., Simplifications of the Bilinear Transfer for Microscopic Binary Objects, Journal of the Optical Society of America, vol. 5, No. 7, Jul. 1998.
Creath, Katherine, Phase-Shifting Speckle Interferometry, Applied Optics, vol. 24, No. 16, Sep. 15, 1985.
Goryachev, D.N. et at, Photographic Process Based on Oxidation-Reduction Reactions on the Surface of Silicon, Soviet Physics—Semiconductors, vol. 4, No. 8, Feb. 1971.
Goryachev, D.N. et al., Photographic Process Based on Oxidation-Reduction Reactions on Thin Films of Lead Sulfide and Selenide, Soviet Physics—Semiconductors, vol. 4, No. 8, Feb. 1971.
Daniele et al., Photoelectric Effect from a Metal Surface: A Revisited Theoretical Model, Journal of the Optical Society of America, vol. 9, No. 10, Oct. 1992.
Dickson et al., Holographic Polarization-Separation Elements, Applied Optics, vol. 33, No. 23, Aug. 10, 1994.
Fujimaki et al., 9 ps Gate Delay Josephson or Gate with Modified Variable Threshold Logic, Japanese Journal of Applied Physics, vol. 24, No. 1, Jan. 1985.
Abdllaev, G.B., Formation of Photographic Images on Thin Films of Gallium and Indium Selenides, Soviet Physics—Semiconductors, vol. 6, No. 6, Dec. 1972.
Gorlin, G.B. et al., Possible Use of the Semiconductor—Dielectric Electrophotographic System in Long-Wavelength Semiconductor Photography, Soviet Physics—Semiconductors, vol. 6, No. 2, Aug. 1972.
Graham Saxby, Practical Display Holography, Chapter 20—"Embossed Holograms" 1988.
Grischkowsky et al., Capacitance Free Generation and Detection of Subpicosecond Electrical Pulses on Coplanar Transmission Lines, Journal of Quantum Electronics, Feb. 1988.
Groh and Marie, Information Input in an Optical Pattern Recognition System Using a Relay Tube Based on the Pockels Effect, Optics Communications, vol. 2, No. 3, Aug. 1970.
Heinrich, H.K. et al., Noninvasive sheet charge density probe for integrated silicon devices, Applied Physics Letters, vol. 48, No. 16, Apr. 1986, p. 1066-1068.
Klocek, Paul ed., Handbook of Infrared Optical Materials, Marcel Dekker, Inc., New York, 1991.
Hariharan, P., Optical Holography: Principles, techniques and applications, 2nd Ed., Cambridge Studies in Modern Optics, Press Syndicate of Cambridge University Press 1996.

(56) References Cited

OTHER PUBLICATIONS

Hariharan, P., Simple Laser Interferometer with Variable Shear and Tilt, Applied Optics, vol. 14, No. 5, May 1975.

Heggarty and Chevalier, Signal Window Minimum Average Error Algorithm for Computer-Generated Holograms, Journal of the Optical Society of America, vol. 15, No. 3, Mar. 1998.

Heinrich et al., "Measurement of Real Time Digital Signals in a Silicon Bipolar Junction Transistor Using a Noninvasive Optical Probe" May 6, 2001.

Yamaguchi, Ichirou et al., Phase-shifting Digital Holography, Optics Letters, vol. 22, No. 16, Aug. 1997.

Ineichen et al., Thermoplastic Film Camera for Holographic Recording of Extended Objects in Industrial Applications, Applied Optics, vol. 21, No. 12, Jun. 15, 1982.

Ivanova, et al., Semiconductor Photographic System Based on High-Resistivity Gallium Arsenide, Soviet Physics-Semiconductors, vol. 6, No. 9, Mar. 1973, pp. 1585-1587.

Jahoda et al., Fractional-Fringe Holographic Plasma Interferometry, Applied Optics, vol. 6, No. 8, Aug. 1967.

Schmidt-Tiedemann, K.J., Stress Optical Constants of Germanium, Philips Research Lab Hamburg, Hamburg, Germany, Letters to the Editor, pp. 2058 & 2059, received Jun. 5, 1961.

Kaminow, I.P. et al., Electrooptic Light Modulators, Proceedings of the IEEE, vol. 54, No. 10, Oct. 1966.

Kewitsch et al., Electric-Field Multiplexing/Demultiplexing of Volume Holograms in Photorefractive Media, Optics Letters, vol. 18, No. 7, Apr. 1, 1993.

Knight, Gordon R., Holographic Associative Memory and Processor, Applied Optics, vol. 14, No. 5, May 1975.

Kolner and Bloom, Electrooptic Sampling in GaAs Integrated Circuits, IEEE Journal of Quantum Electronics, vol. QE-22, No. 1, Jan. 1986.

Kotani et al., 5.6 ps Gate Delay All Refractory Josephson or Gate with Modified Variable Threshold Logic, Japanese Journal of Applied Physics, vol. 24, No. 6, Jun. 1985.

\* cited by examiner

MULTIPLE BEAM TRANSMISSION INTERFEROMETRIC TESTING METHODS FOR THE DEVELOPMENT AND EVALUATION OF SUBWAVELENGTH SIZED FEATURES WITHIN SEMICONDUCTOR AND ANISOTROPIC DEVICES

CROSS REFERENCE TO RELATED APPLICATIONS

This application is a continuation of U.S. application Ser. No. 13/903,232, filed May 28, 2013, which is a continuation of U.S. application Ser. No. 13/366,180, filed Feb. 3, 2012, now U.S. Pat. No. 8,462,350 issued Jun. 11, 2013, which is a continuation of U.S. application Ser. No. 12/779,749, filed May 13, 2010, now U.S. Pat. No. 8,139,228 issued Mar. 20, 2012, which is a continuation of U.S. application Ser. No. 12/120,924, filed May 15, 2008, now U.S. Pat. No. 7,733,499 issued Jun. 8, 2010, which is a continuation of U.S. application Ser. No. 11/278,389, filed Mar. 31, 2006, now U.S. Pat. No. 7,400,411 issued Jul. 15, 2008, which is a continuation of U.S. application Ser. No. 10/301,030, filed Nov. 20, 2002, now U.S. Pat. No. 7,206,078 issued Apr. 17, 2007, which claims the benefit of U.S. Provisional Application No. 60/337,419, filed Dec. 6, 2001.

BACKGROUND OF THE INVENTION

1. Field of the Invention

The present invention relates to non-invasive testing.

The development of advanced integrated circuit devices and architectures has been spurred by the ever increasing need for speed. For example, microwave, fiber optical digital data transmission, high-speed data acquisition, and the constant push for faster digital logic in high speed computers and signal processors has created new demands on high-speed electronic instrumentation for testing purposes.

2. Description of Related Art

Conventional test instruments primarily include two features, the integrated circuit probe that connects the test instrument to the circuit and the test instrument itself. The integrated circuit probe has its own intrinsic bandwidth that may impose limits on the bandwidth achievable. In addition, the probe also determines an instrument's ability to probe the integrated circuit due to its size (limiting its spatial resolution) and influence on circuit performance (loading of the circuit from its characteristic and parasitic impedances). The test instrument sets the available bandwidth given perfect integrated circuit probes or packaged circuits, and defines the type of electric test, such as measuring time or frequency response.

Connection to a test instrument begins with the external connectors, such as the 50 ohm coaxial Kelvin cable connectors (or APC-2.4). The integrated circuit probes provide the transitions from the coaxial cable to some type of contact point with a size comparable to an integrated circuit bond pad. Low-frequency signals are often connected with needle probes. At frequencies greater than several hundred megahertz these probes having increasing parasitic impedances, principally due to shunt capacitance from fringing fields and series inductance from long, thin needles. The parasitic impedances and the relatively large probe size compared to integrated circuit interconnects limit their effective use to low-frequency external input or output circuit responses at the bond pads.

Therefore, electrical probes suffer from a measurement dilemma. Good high-frequency probes use transmission lines to control the line impedance from the coaxial transition to the integrated circuit bond pad to reduce parasitic impedances. The low characteristic impedance of such lines limits their use to input/output connections. High-impedance probes suitable for probing intermediate circuit nodes have significant parasitic impedances at microwave frequencies, severely perturbing the circuit operation and affecting the measurement accuracy. In both cases, the probe size is large compared to integrated circuit interconnect size, limiting their use to test points the size of bond pads. Likewise sampling oscilloscopes, spectrum analyzers, and network analyzers rely on connectors and integrated circuit probes, limiting their ability to probe an integrated circuit to its external response. For network analysis, a further issue is de-embedding the device parameters from the connector and circuit fixture response, a task which grows progressively more difficult at increasing frequencies.

With the objective of either increased bandwidth or internal integrated circuit testing with high spatial resolution (or both) different techniques have been introduced. Scanning electron microscopes or E-beam probing uses an electron beam to stimulate secondary electron emission from surface metallization. The detected signal is small for integrated circuits voltage levels. The system's time resolution is set by gating the E-beam from the thermionic cathodes of standard SEM's. For decreasing the electron beam duration required for increased time resolution, the average beam current decreases, degrading measurement sensitivity and limiting practical systems to a time resolution of several hundred picoseconds. Also, SEM testing is complex and relatively expensive.

Valdmanis et al., in a paper entitled "Picosecond Electronics and Optoelectronics", New York: Springer-Verlag, 1987, shows an electro-optic sampling technique which uses an electrooptic light modulator to intensity modulate a probe beam in proportion to a circuit voltage. Referring to FIG. 1, an integrated circuit 10 includes bonded electrical conductors 12 fabricated thereon whereby imposing differential voltages thereon gives rise to an electric field 14. For carrying out a measurement an electro-opti needle probe 16 includes an electro-optic tip 18 (LiTaO$_3$) and a fused silica support 20. A light beam incident along path 22 is reflected at the end of the electro-optic tip 18 and then passes back along path 24. An electric field 14 alters the refractive index of the electro-optic tip 18 and thereby alters the polarization of the reflected light beam on the exit path 24, which thus provides a measure of the voltages on the conductors 12 at a single point. Unfortunately, because of the proximity of the probe 16 to the substrate 10 capacitive loading is applied to the circuit, thereby altering measurements therefrom. In addition, it is difficult to position the probe 16 in relation to the conductor because the probe 16 and circuit 10 are vibration sensitive. Also, the measurements are limited to conductors 12 on or near the surface of the circuit 10. Further, the circuit must be active to obtain meaningful results and the system infers what is occurring in other portions of the circuit by a local measurement.

Weingarten et al. in a paper entitled, "Picosecond Optical Sampling of GaAs Integrated Circuits", IEEE Journal of Quantum Electronics, Vol. 24, No. 2, February 1988, disclosed an electro-optic sampling technique that measures voltages arising from within the substrate. Referring to FIG. 2, the system 30 includes a mode-locked Nd:YAG laser 32 that provides picosecond-range light pulses after passage through a pulse compressor 34. The compressed pulses are passed through a polarizing beam splitter 36, and first and second wave plates 38 and 40 to establish polarization. The polarized light is then directed at normal incidence onto an integrated circuit substrate 42. The pulsed compressed beam can be focused either onto the probed conductor itself (backside probing) or onto the ground plane beneath and adjacent to the probed conductor (front-side probing). The reflected light from the substrate is diverted by the polarizing beam splitter 36 and detected by a single point slow photo diode detector 44. The photo diode detector is also connected to a display 46.

A microwave generator 48 drives the substrate 42 and is also connected to an RF synthesizer 50, which in turn is connected to a timing stabilizer 52. The pulse output of the laser 32 is likewise connected to the timing stabilizer 52. The output of the stabilizer 52 connects back to the laser 32 so that the frequency of the microwave generator 48 locks onto a frequency that is a multiple of the laser repetition rate plus an offset. As a consequence, one may analyze the electric fields produced within the integrated circuit as a result of being voltage drive, thus providing circuit analysis of the integrated circuit operation. In essence, the voltage of the substrate imposed by the microwave generator 48 will change the polarization in the return signal which results in a detectable change at the diode detector 44.

Referring to FIGS. 3A and 3B, the locations along the incident beam are designated a, b, c (relative to the "down" arrow), and designated along the reflected beam as d, e, and f (relative to the "up" arrow), and the intensity modulated output signal is designated as g. The corresponding states of polarization exhibited in the measurement process are shown in the similarly lettered graphs of FIG. 3B. At location a of FIG. 3A, the polarizing beam splitter 36 provides a linearly polarized probe beam (as shown in graph a of FIG. 3B) that is passed through the first wave plate 38, which is a T/2 plate oriented at 22.5 degrees relative to the incident beam polarization, so as to yield at location b the 22.5 degree elliptically polarized beam shown in graph b of FIG. 3B). The beam then passes through the second wave plate 40, which is a T/2 plate oriented at 33.75 degrees relative to the incident beam, so as to rotate the beam an additional 22.5 degrees to yield at location c the 45 degree polarization (shown in graph c of FIG. 3B), which is at 45 degrees to the [011] direction of the substrate 42, i.e., the cleave plane of the wafer. Similar rotations are shown for the reflected beam at the successive locations d, e, and f, the resultant polarizations respectively being as shown in graphs d, e, and f of FIG. 3B. As shown in graph f in particular, the electro-optic effect of any voltage present on the substrate 42 at the spot at which the beam reflects therefrom brings about a change in the specific polarization orientation in an amount designated in graph f of FIG. 3B as &, and that change is reflected in an amplitude change or intensity modulation in the output signal at location g that passes to the photo-diode 44 (as shown in graph g of FIG. 3B). It is the measurement of & that constitutes the voltage measurement. Among the various techniques of pre-determining the voltage patterns to be used in testing an integrated circuit, or indeed an entire printed circuit, Springer, U.S. Pat. No. 4,625,313, describes the use in a CPU of a ROM "kernel" in which are stored both a test program sequence and the testing data itself.

Since the system taught by Weingarten et al. does not include a probe proximate the circuit under test the limitations imposed by capacitive loading of the circuit to be tested is avoided. However, the system taught by Weingarten et al. is limited to "point probing," by the lens 41 converging the input beam into a test point on the order of one wavelength. Unfortunately, to test an entire circuit an excessive number of tests must be performed. In addition, it is not possible to test multiple points simultaneously without the use of multiple systems, which may be useful in testing different portions of the circuit that are dependent upon one another. The resulting data from the system is presented to the user as a single amplitude measurement, i.e., the intensity of the signal produced at the photo-diode 44 depends simply upon the degree to which the polarization of the reflected light entering the beam splitter 36 has been rotated, so that not only are the actual phase and polarization data that derive the reflection process lost, but the precision and accuracy of the measurement becomes subject to the linearity and other properties of the photo-diode 44 and the display 46.

Various other techniques by which semiconductors may be characterized, using electromagnetic radiation of different wavelengths under different conditions is cataloged by Palik et al. in "Nondestructive Evaluation of Semiconductor Materials and Device," Plenum Press, New York, 1979, chapter 7, pp. 328-390. Specifically, treatment is given of (1) infrared reflection of GaAs to obtain the optical parameters n and k and then the carrier density N and mobility u; (2) infrared transmission in GaAs to determine k from which is determined the wavelength dependence of free carrier absorption; (3) infrared reflection laser (spot size) scanning of and transmission through GaAs to determine free carrier density in homogeneity, including local mode vibrations; (4) far infrared impurity spectra; (5) infrared reflection and transmission from thin films on a GaAs substrate; microwave magnetoplasma reflection and transmission; (6) submillimeter-wave cyclotron resonance in GaAs to determine magnetotransmission; (7) ruby laser radiation to form a waveguide in a GaAs film on a GaAs substrate, the propagation features of which are then measured using infrared radiation; (8) infrared reflectance from multilayers of GaAs on a GaAs substrate; (9) reflectance measurements of graded free carrier plasmas in both PbSnTe films on PbSnTe substrates and InAs on GaAs substrates; (10) interferometric measurements of ion implanted layers; (11) infrared restrahlen spectra, also to determine lattice damage effects; (13) ellipsometric measurements of ion-implanted GaP; (14) determination of optical constants by internal reflection spectroscopy; (15) laser raster scanning of semiconductor devices to measure photoconductivity, to track the flow of logic in a MOS shift register (because of current saturation, the effect of the laser light differs in cells in the 0 or 1 logic state), and with a more intense laser power level to change those logic states (i.e., to write to the circuit); (16) laser raster scanning of semiconductor devices to determine variations in resistivity and carrier lifetimes; (17) thermal imaging of circuits to find hot spots; (18) Raman backscattering to determine free carrier density; (19) carrier injection to study the band edge; (20) birefringence measurements in monolayers of GaAs and AlAs on GaAs to characterize the resultant strain; (21) photoluminescence and cathodoluminescence measurements of implanted layers and acceptor and donor densities. With the exception of (7) above which relates to waveguide transmission, and also of (15) and (17), these techniques relate to the characterization of static systems. While (15) relates to a spot canning technique of the operational integrated circuit and (17) relates to hot-characterization of the device temperature.

BRIEF SUMMARY OF THE INVENTION

What is desired, therefore, is a high bandwidth non-invasive testing system for semi-conductor materials.

DETAILED DESCRIPTION OF THE INVENTION

Figure 1:
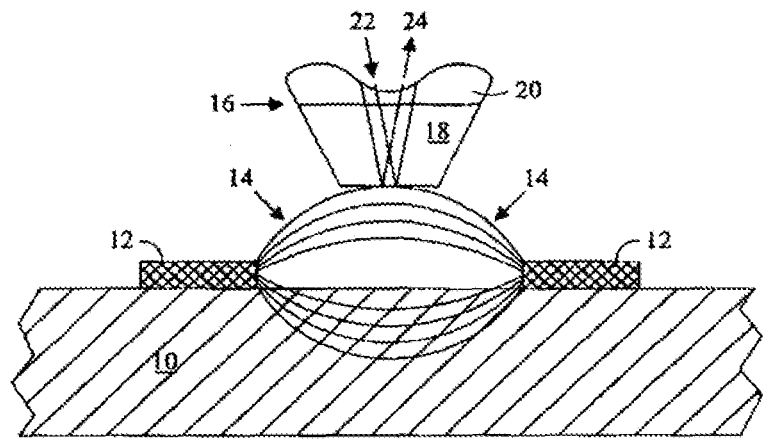
FIG. 1 illustrates an electro-optic sampling technique using electro-optic light modulator.
Figure 2:
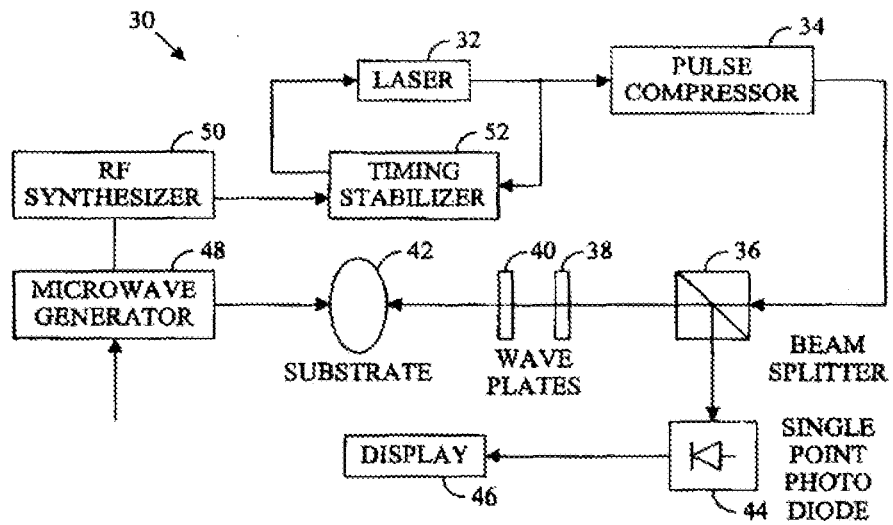
FIG. 2 illustrates a single point detection system.
Figure 3B:
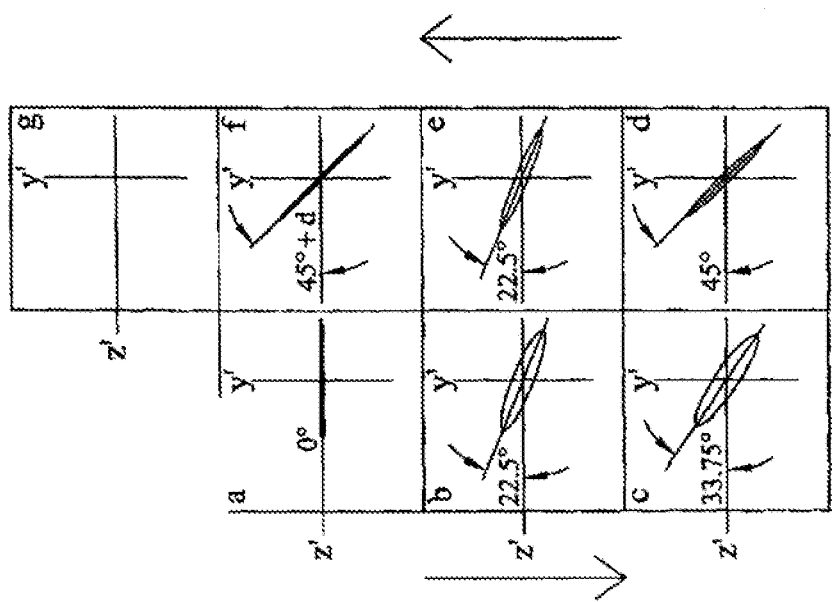
FIGS. 3A and 3B illustrate the beams of FIG. 2.
Figure 3A:
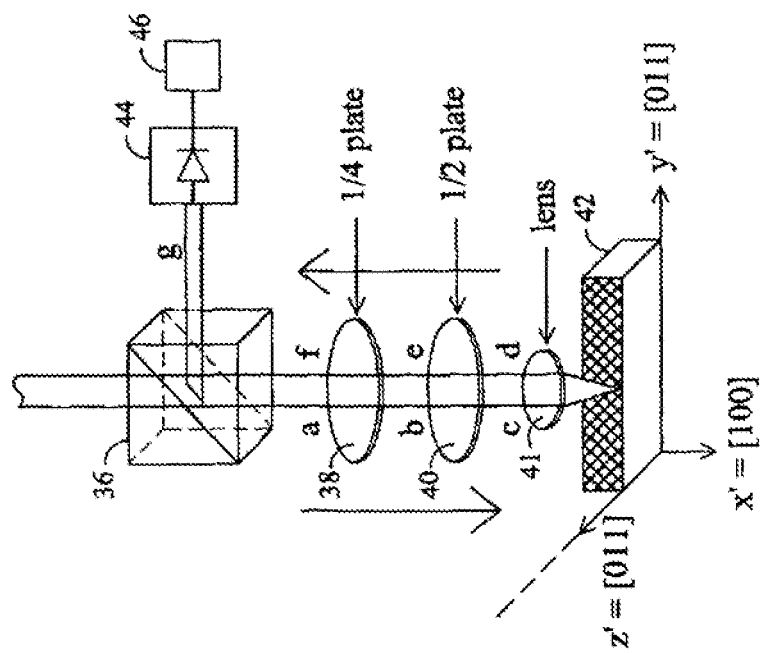

The present inventors came to the realization that the single point non-invasive probing technique of semiconductor materials could be enhanced if an area significantly greater than a wavelength of the optical test signal could be transmitted through or reflected off of a semiconductor material. Semiconductor materials generally exhibit electro-optic or photo-refractive effects, which can be made to become birefringent by the application of an electric field, either as such or as embodied in electromagnetic radiation. The present inventors then came to the realization that if an object in a state in which it is not birefringent, but such birefringence can then be brought about by electrical or electromagnetic techniques, the nature of the birefringence so introduced can be studied to determine characteristics of the material. Upon further consideration the present inventors then came to the realization that interferometry techniques can sense a wide region, such as that passing through or reflected off a semiconductor material, which can then be analyzed.

An interference pattern is created by a coherent light beam being transmitted through or reflected from an object onto a recording medium or otherwise a sensing device, which at the same time the original beam is also directed onto that recording medium or otherwise sensing device as a reference beam. Various characteristics of the resultant transmitted or reflected beam, herein called the "object wave," are recorded in the resultant interference pattern between the object wave and the reference beam. That is to say, inasmuch as the intensities of the reference beam and the object wave have been recorded in that interference pattern, the resulting pattern typically includes a set of fringes as a result of the applied voltage. Those characteristics are in part a consequence of the physical structure (i.e., "appearance") of the object, hence the interference pattern is related to the structure of the object.

The present inventors also realized that particular semiconductor materials are generally transparent to light of particular wavelengths so that the light may freely pass through and reflect back though the semiconductor, or otherwise pass through the semiconductor, substantially unaffected when the semiconductor is not stressed, such as by no applied voltage. Likewise, when the semiconductor material, such as an integrated circuit, is stressed by applying a voltage therein by energizing a circuit fabricated therein, the same light will reflect or otherwise pass through the semiconductor material, while being affected by the changes imposed by the applied voltage, such as birefringence, thereby resulting in a different pattern. The stressed and unstressed states can be recorded as different interferometry images. The two interferometry images may then be compared to one another to determine the actual operating characteristics within the semiconductor material. Also, two different stressed states of the semiconductor material may be obtained and thereafter two interferometry images, both from stressed states, may be compared to one another. In addition, by its nature, interferometry techniques record a significant spatial region much larger than a single wavelength simultaneously which is important for characterizing regions of the semiconductor material. For example, the operational characteristics of two different regions may be interrelated which is unobtainable using techniques limited to a single wavelength in "spot size." The present inventor's realization that the application of interferometry techniques for the testing of semiconductor devices was only after at least the culmination of all of the aforementioned realizations.

Of particular interest is the "real time" characterization of operating characteristics of integrated circuits where such birefringence is introduced by the electro-optic effect, i.e., the imposition of a voltage onto the object (as in the ordinary operation of the integrated circuit) causes birefringence therein. In other words, upon application of an electric field the material, such as GaAs or silicon, introduces an anisotropy and the ordinary complex refractive index n* of the material is decomposed into $n_o^*$ and $n_e^*$ components. Another technique applicable to appropriate substrates whether or not any operational voltages are also applied thereto, lies in utilization of the photo-refraction effect, wherein electromagnetic radiation of a required intensity is illuminated onto the substrate, and a birefringence or change in birefringence is then brought about. Inasmuch as semiconductor and like materials are generally characterized by a wavelength threshold below which photo-refraction will occur, but above which no photo-refraction takes place, this latter mode of operation employs electromagnetic radiation of differing wavelengths, first to bring about a desired photo-refractive effect, and then secondly to analyze the effect so brought about.

Figure 4:
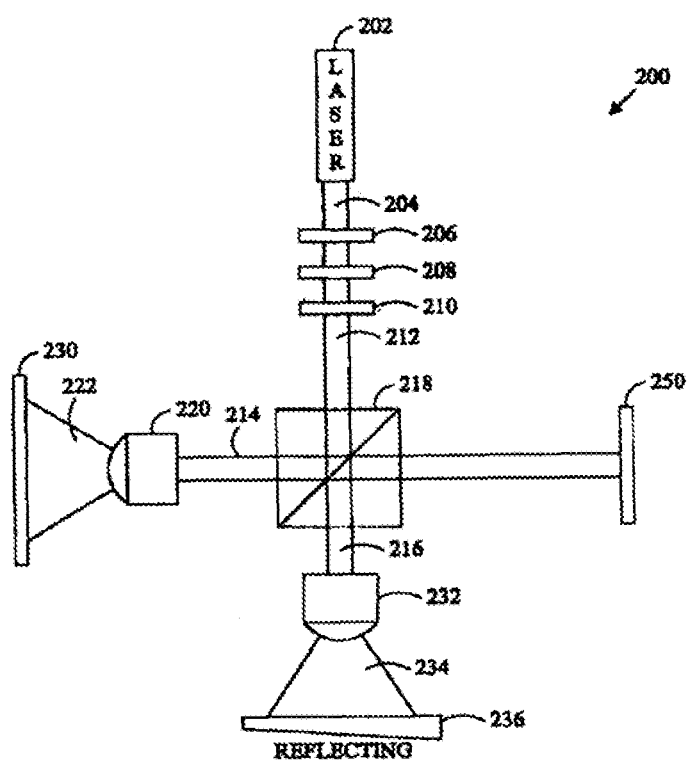
FIG. 4 illustrates one optical system for non-destructive wave front testing of a device under test.

FIG. 4 shows an interferometry apparatus 200 comprising a laser 202 such as a infrared DFB laser diode or the like, from which is derived a plane wave of linearly polarized light 204. The optical path thus defined may optionally include a selected first neutral density filter 206 that permits convenient adjustment of the laser power level. Likewise, the beam intensity may be varied by the applied voltage level. The beam 204 from the laser 202 (or from the filter 206, if used) may then be passed into a first broad band polarization rotator 208 for purposes of placing the plane of polarization of the laser beam at a desired orientation. Whether or not the polarization rotator 208 is used, the beam may then be passed through one or more first wave plates 210 that may optionally be used to establish a desired degree of ellipticity in the beam. Further, the wave plates may likewise establish with the beam is non-diverging/non-converging, diverging, or converging. In any case, the resultant beam 212 is then separated into a pair of beams 214 and 216 by a beam splitter 218. The beam splitter 218 may alternatively be any device suitable to separate the beam 212 into multiple beams. Likewise, components or beams 214 and 216 are interchangeable.

The beam 214 may pass through a first lens 220 that will then yield an expanded and/or expanding plane wave 222. The plane wave 222 is then incident on a device under test 230. The plane wave 218, having a wavelength suitable to pass through semiconductor material, passes through either the front side or the back side (or the edge) of the surface of the device under test 230 and reflects from the interior structures within the device under test 230. As a result of beam 222 being reflected back from the device under test 230, the reflected beam will pass back onto beam splitter 218 so as to be passed towards and ultimately impinge upon a recording device 250. The recording device 250 may be any suitable type of sensing device, such as for example, a charge coupled device.

Similarly, the beam 216 may pass through a second lens 232 that will then yield an expanded and/or expanding plane wave 234. The plane wave 234 is then incident on a reflecting device 236. The plane wave 218, having a wavelength suitable to pass through semiconductor material, reflects from a reflecting device 236. As a result of beam 234 being reflected back from the reflecting device 236, the reflected beam will be reflected by the beam splitter 218 so as to be passed towards and ultimately impinge upon the recording device 250.

Since both the reference beam (second beam 234) and the object beam (object beam 222) derive from a common, preferably coherent source (laser 202) and are simultaneously, or substantially simultaneously, incident on the recording device 250, the favorable conditions for forming an interference pattern are present. One or more of the lenses may be omitted, as desired. Also, the object and reference beams may be reversed relative to the beam splitter, as desired. It is likewise to be understood that one or more light sources may be used, as desired. Also, it is to be understood that more or more recording devices may be used, as desired. In addition, it is to be understood that the recording device(s) may record the object beam and the reference beam independently of one another, which are thereafter combined in a suitable manner to generate an interference wave front pattern.

For purposes of the present invention, and in taking an initial interference, the device under test may be any suitable device to which the characteristics are desired, such as for example, a functional integrated circuit on which the surface has been exposed (i.e., potting is not present) but to which no voltages or other external stimuli have been applied, a semiconductor material such as a wafer taken from or existent within a wafer manufacturing line, a semiconductor wafer taken from or existent within a chip manufacturing line at any of various stages of manufacture (deposition, etching, metallization, etc.) or the like, the recording device may be taken to be any suitable material for recording or otherwise sensing an interference image, such as for example, a photographic film, charge coupled device, or thermoplastic plate onto which the initial interference pattern is recorded in the graphic film, charge coupled device, or thermoplastic plate onto which the initial interference is sensed and/or recorded.

As to the case in which the device under test is a functional but not energized integrated circuit, a first interference may be recorded therefrom using the apparatus as shown in FIG. 4, i.e., the interference pattern is recorded either onto photographic film, charge coupled device, or within a thermoplastic plate. A second interference may then be made of that same to recording device while either being energized with a voltage or current, or illuminated with light of a wavelength shorter than the characteristic threshold wavelength for the material. In the case in which the device under test is a semiconductor wafer, a first interference may similarly be recorded/sensed and then a second interference may be recorded/sensed while illuminating the wafer in the manner just stated. In either case, any birefringence effects brought about either by the electro-optic effect or by the photo-refractive effect will then be recorded/sensed. A comparison of the two interferences, both taken from one or the other instance of the device under test, will isolate such electro-optically or photo-refractively produced birefringence.

It is preferred to employ a CCD camera as the sole recording device whereby the first and indeed a multiplicity of subsequent interference patterns may be recorded, at rates commensurate with the rates of operation of an integrated circuit itself, i.e., 50 MHZ or more in terms of charge coupled device operation. An additional advantage in using only the CCD camera for recording interference is that the "reference" interference, i.e., the interference recorded from the device under test (either as an IC or as a semiconductor wafer) at a time that no voltages or birefringence-inducing laser light was applied thereto, will be recorded digitally as well, and comparisons between the reference and subsequent interferences may be made by means other than within the experimental apparatus itself. i.e., by ordinary digital signal processing (DSP).

For the purpose of processing such a data stream an analyzer connected to the recording device, and then a monitor connecting to analyzer. Inasmuch as the laser source in the present embodiment is preferably a DBF infrared laser diode (e.g., 900 nm-1600 nm, or 1000 nm-1500 nm, or 2000 nm-14,000 nm), the data to be analyzed may be generated by means of triggering the recording of CCD images in synchrony with the imposition of particular voltage data onto the test object, which may be an IC or possibly an entire printed circuit. As noted previously, the Springer patent describes the use of a digital "kernel" comprising a predetermined test program together with the digital data to be employed by that program, both of which are stored in ROM. The Springer apparatus then uses voltage probes and the like applied to various circuit nodes to test circuit performance in a "manual" fashion; the present invention, of course, in addition permits an "automatic" process of testing an entire IC, circuit board or a semiconductor wafer at any desired stage of manufacture.

During operation a first interference pattern, stressed or unstressed, may be obtained with the "fringes" around a particular feature of interest identified. With changes in the applied voltage and/or field the location and/or density of the fringes will vary. However, with slight changes in the fields the exact applied field and/or voltage may be difficult at times to determine. The determination may be assisted by understanding the material's optical properties and physical characteristics (e.g., thickness, layout, doping profile, shape, etc.). Accordingly, the reflecting device 236 may include an adjustment mechanism to vary the location and/or angle of the reflecting device 236 with respect to the beam incident thereon. By varying the position of the reflecting device 236 the location of the fringes may be modified, such as to line up with respect to a feature, such as a conductor. Thereafter a second interference pattern, stressed or unstressed, may be obtained with the "fringes" around a particular feature of interest identified. The change in the fringes between the two states, together with known characteristics of the particular materials within the device under test in the region of interest, may be used to determine the voltage or relative voltage change within the material in the region of interest. Similarly, the change in the wave front fringes between the two states, together with known voltages or relative voltage change, may be used to characterize the particular materials within the device under test in the region of interest. The change in the wave front fringes may be determined, for example, by subtraction, by addition, or any other suitable image comparison operation. It would likewise be noted that many such operations, such as subtraction, are capable of resolving features less than one wavelength in size. In addition, changes in the wave front fringes with known devices, using VLSI or VHDL circuit coordinate maps (or the like) may be used to characterize voltages and voltage changes. This permits for the observation of voltages within individual devices such as transistors or analysis of device registers or individual values of larger structures such as a micro-controller, or characterize fringes within the doped and non-doped conductive, semi-conductive, and non-conductive material (e.g., dielectric material) adjacent conductors, non-conductors, or semi-conductor material, or the like. Also, this technique may be used to study the effects of incident radiation, such as radio waves, x-rays, magnetic fields, chemical solutions upon the materials, etc.

It will be understood by those of ordinary skill in the art that other arrangements and disposition of the aforesaid components, the descriptions of which are intended to be illustrative only and not limiting, may be made without departing from the spirit and scope of the invention, which must be identified and determined only from the following claims and equivalents thereof.

Figure 5:
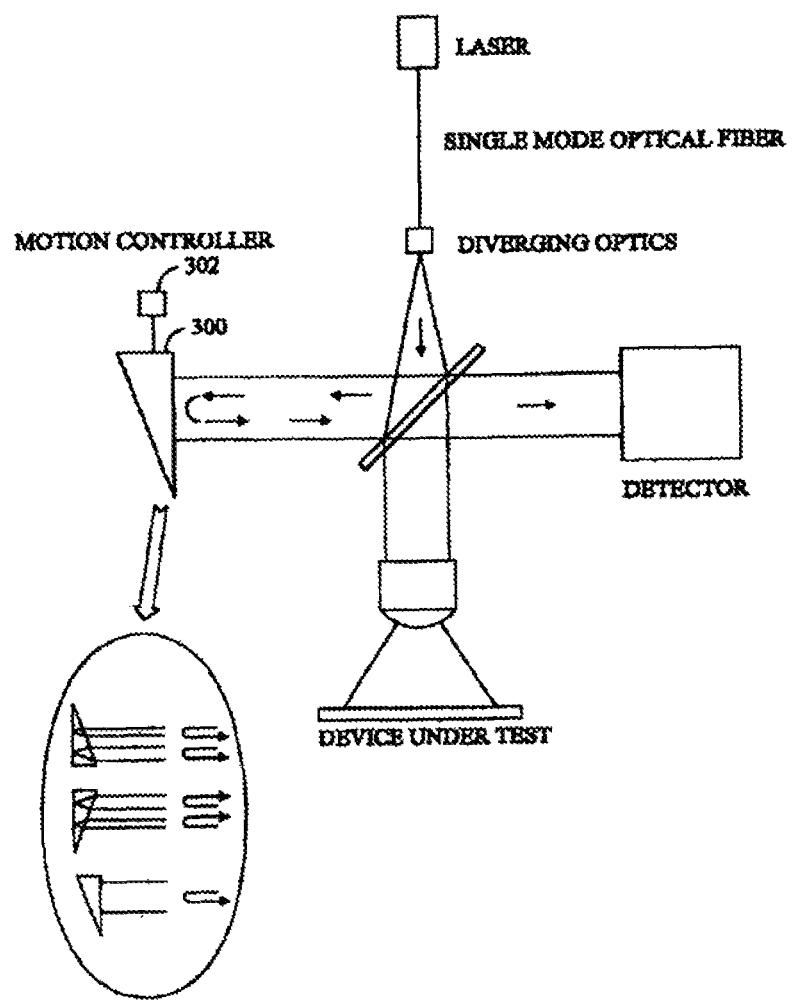
FIG. 5 illustrates another optical system for non-destructive wave front testing of a device under test.

Referring to FIG. 5, another alternative design for the optical system is illustrated for introducing an additional spatial shifting feature to the system. In the reference beam path an spatial beam adjustment member 300 is included. The spatial beam adjustment member 300 spatially offsets the reflected beam relative to the incident beam. In addition, the spatial beam adjustment member 300 may likewise be adjustable to any suitable angle. By recording the interference patterns at multiple different angles, for the same object beam, and processing the same as previously described you may obtain parallax information. In essence, this parallax information provides some three-dimensional information with respect to the structure and voltages within the device under test.

The invention claimed is:

1. A method for developing and evaluating semiconductor or anisotropic devices or wafers for manufacture by optical interferometric testing and displaying internal stresses of semiconductor or anisotropic devices or wafers and for testing semiconductor or anisotropic devices or wafers while being manufactured, the device or wafer under test being comprised a semiconductor conductor or anisotropic material having an interior surface and interior structures, comprising:

using a holographic optical interference system with at least one light source, providing at least one light beam of coherent wavelength with a wavelength to which the semiconductor or anisotropic material is at least semi-transparent or transparent, splitting the light beam into a pair of beams, comprising a reference beam and an object beam, imposing and adjusting the polarization of the object beam on the exterior surface of the semiconductor or anisotropic material to generate a transmission object beam transmitted through the device under test having a polarization from the interior structures of the semiconductor or anisotropic material and interior surfaces of the semiconductor or anisotropic material to generate a transmitted polarized beam passing through the interior structures of the semiconductor or anisotropic material, adjusting at least one of the following attributes of the angle of incidence or polarization or the length of the converging or diverging optical pathway of the reference beam relative to the object beam between one or more angles with the semiconductor or anisotropic material being in one or more states for each angle of the reference beam, or adjusting at least one of said attributes of the transmitted object beam relative to the incident reference beam, imposing the transmitted object beam and the reference beam onto one or more detection devices to create a plurality of interference or interferometric patterns of the transmitted object beam with the incident reference beam, one interference or interferometric pattern at each of the plurality of angles of the reference beam, varying the magnification or optical pathway of the incident reference beam relative to the magnification of the object beam passing through the device, feature, or area under test, using one or more detection devices to physically record or digitally store the plurality of interference or interferometric patterns of one or more infrared or thermal wavelengths, comparing the plurality of interference or interferometric patterns to one another to determine or calculate and display stress or the effects of such stress and interior structure characteristics within the semiconductor or anisotropic material, device or wafer, and using the plurality of interference or interferometric patterns comprising of the interference of one or more differing infrared or thermal wavelengths to perform at least one of the following:

(1) test, shape, calculate or determine semiconductor or anisotropic materials, devices, features, wafers or interior structures, (2) evaluate, monitor, or calculate internal processes in semiconductor or anisotropic materials, devices, features, or wafers, (3) test integrated circuits, devices, features, or materials, (4) determine or calculate the effects of electromagnetic signals that act upon or within the semiconductor or anisotropic wafers, dielectric materials, conductors, and within materials adjacent to, the feature, devices or processes, (5) determine or calculate at least one effect of energies or signals acting upon or within the semiconductor or anisotropic materials, dielectric materials, conductors, and within materials adjacent to, devices, features, or wafers, (6) monitor, evaluate, calculate or determine the effectiveness or efficiency of the processes or materials to create semiconductor or anisotropic materials, devices, features, wafers or interior structures, or (7) determine or calculate the effects of changes to process, configuration, or materials and identify or calculate at least one change that affects the semiconductor or anisotropic materials, devices, features, wafers or interior structures.

2. The method of claim 1, wherein the object beam passes into the interior or device or material under test and the object beam reflects back through the interior of the device or material under test.

3. The method of claim 1, wherein at least one of the states of the semiconductor material is an external stress, the external stress or the effects of the external stress being produced by imposing incident voltages or chemical solutions upon or within at least one of the following: the semiconductor material, dielectric materials, conductors, and within materials adjacent to, the feature, device or wafer.

4. The method of claim 1, wherein at least one of the states of the semiconductor material is an external stress, the external stress or the effects of the external stress being produced by imposing incident radio waves upon or within at least one of the following: the semiconductor material, dielectric materials, conductors, and within materials adjacent to, the feature, device or wafer.

5. The method of claim 1, wherein at least one or more detector devices records a plurality of interference patterns of a plurality of one or more external stresses or the effects of the external stresses which produce a change in the state of the refractive indexes or birefringence states upon or within at least one of the following: the semiconductor material, dielectric materials, conductors, and within materials adjacent to, the feature, device or wafer.

6. The method of claim 1, wherein the magnification or length of the optical pathway of the reference beam is adjusted to be converging or diverging to the object beam to enhance the visibility or contrast of the interference or interferometric pattern with respect to a feature of at least one of the following: the semiconductor material, dielectric materials, conductors, and within materials or adjacent to, the feature, device or wafer.

7. The method of claim 1, wherein the diameter of the object beam is selected to produce a spatial region on the exterior surface of the semiconductor material equal to or larger than the focal or spot size of a single wavelength of the object beam.

8. The method of claim 1, wherein at least one or more detection devices physically records or digitally stores the plurality of interference or interferometric patterns or, one or more detectors records at least one of the states of the semiconductor or anisotropic material is an external stress or the effects of the external stress detected or displayed or calculated by means of triggering the recording or storage device of a plurality of interference patterns in synchrony with the imposition of a plurality of one or more external or internal stresses or the effects of said stresses or electromagnetic signals or the effects of the electromagnetic signals or external stresses acting upon or within at least one of the following: the semiconductor or anisotropic material, dielectric materials, conductors, and within materials adjacent to, the feature, device or wafer.

9. The method of claim 1, wherein at least one of the states of the semiconductor material is an external stress or signal, the external stress or the effects of said stress or signals being produced by imposing incident x-rays acting upon at least one of the following: the semiconductor material, dielectric materials, conductors, and within materials adjacent to, the feature, device or wafer.

10. The method of claim 1, wherein at least one of the states of the semiconductor material is an external stress or signal, the external stress or the effects of the external stress or signals being produced by incident magnetic fields acting upon at least one of the following: the semiconductor material, dielectric materials, conductors, and within materials adjacent to, the feature, device or wafer.

11. The method of claim 1, wherein at least one of the states of the semiconductor material is an external stress, the external stress or the effects of the external stress being produced by incident chemical solutions acting upon at least one of the following: the semiconductor material, dielectric materials, conductors, and within materials adjacent to, the feature, device or wafer.

12. The method of claim 1, wherein the magnification or polarization or length of the optical pathway of the reference beam is adjusted to be converging or diverging to the object beam to enhance the visibility of the interference or interferometric pattern with respect to a feature of the semiconductor material, device or wafer, and wherein automatic digital signal or image processing displays or calculates the plurality of one or more image detection devices simultaneously monitoring or calculating the feature or internal surface or the effects of signals upon at least one of the following: the semiconductor material, dielectric materials, conductors, and within materials adjacent to, the feature, device or wafer.

13. The method of claim 1, wherein the magnification or polarization or length of the optical pathway of the reference beam is adjusted to be converging or diverging to the object beam to enhance the visibility or contrast of the interference or interferometric pattern with respect to a feature of the semiconductor material, device or wafer, and wherein automatic digital signal or image processing processes or calculates the plurality of interference patterns and displays or calculates the plurality of internal stresses or the effects of the internal stresses or signals within the semiconductor material, dielectric materials, conductors, and within materials adjacent to, the feature, device, wafer or feature at a desired stage of development or manufacture.

14. The method of claim 1, wherein the magnification or polarization or length of the optical pathway of the reference beam is adjusted to be converging or diverging to the object beam to enhance the visibility or contrast of the interference pattern with respect to a feature of the semiconductor material, device or wafer, and wherein the detection device records or digitally stores changes in the plurality of interference or interferometric patterns to characterize and display or calculate at least one internal stress or the effects of the internal stress, or display and characterize one signal and the effects of the signal.

15. The method of claim 1, wherein the magnification or polarization or length of the optical pathway of the reference beam is adjusted to be converging or diverging to the object beam to enhance the visibility or contrast of the interference or interferometric pattern with respect to a feature of the semiconductor material, dielectric materials, conductors, and within materials or adjacent to, the feature, device or wafer, and wherein the interference or interferometric patterns are compared by digital signal or image processing with an electronic circuit coordinate map to determine or calculate and display at least one internal stress or the effects of the internal stress of a feature or an interior surface or structures within the semiconductor material or external stress or stresses or signals acting upon at least one of the following: the semiconductor material, dielectric materials, conductors, and within materials adjacent to, the feature, device or wafer.

16. The method of claim 1, wherein the diameter of the focal or spot size of the wavelength of the reference-beam is selected to produce an interference or interferometric pattern within the-spatial region on the exterior surface of the semiconductor material equal to, smaller than, or larger than the focal or spot size of a the wavelength of the object beam.

17. The method of claim 1, wherein the diameter of the focal or spot size of the wavelength of the reference-beam is smaller than, or equal to, or larger than the object beam and is selected to produce an photo-carrier induced interference or interferometric pattern within the-spatial region on the exterior surface of the semiconductor material equal to, smaller than, or larger than the focal or spot size of a the wavelength of the object beam.

18. The method of claim 1, wherein one or more object beams passes into the interior or device or material under test and the object beam reflects back through the interior of the device or material under test.

19. A method for developing and evaluating semiconductor or anisotropic devices or wafers for manufacture by optical interferometric testing and displaying internal stresses of semiconductor or anisotropic devices or wafers, or testing semiconductor or anisotropic devices or wafers while being manufactured, the device or wafer under test being comprised of a semiconductor or anisotropic material having an exterior surface and interior structures, using an optical interferometric system with at least one light source providing at least one light beam of coherent wavelength with a wavelength to which the semiconductor or anisotropic material is at least semi-transparent or transparent, the method comprising, imposing and adjusting the polarization of the object beam on the exterior surface of the semiconductor or anisotropic material to generate a transmission object beam having a polarization from the interior structures of the semiconductor or anisotropic material and interior surfaces of the semiconductor or anisotropic material to generate an incident polarized beam passing through the interior surfaces of the semiconductor or anisotropic material, adjusting the angle or length of the optical pathway of a converging or diverging reference beam relative to an object beam between a plurality of angles with the semiconductor or anisotropic material being at least one state for each angle of the reference beam, or adjusting said attributes of the object beam relative to the reference beam, imposing the object beam passing through the device under test and the reference beam onto one or more detection devices to create a plurality of interference or interferometric patterns of the transmitted object beam with the reference beam, at least one at each of the plurality of angles or polarizations of the reference beam, comparing the plurality of interference or interferometric patterns to one another at one or more infrared or thermal wavelengths, or a combination thereof, to determine or calculate characteristics within the semiconductor or anisotropic material, device or wafer, and using the plurality of interference or interferometric patterns to perform at least one of the following:
(1) test, shape, calculate or determine the semiconductor or anisotropic materials, devices, wafers or interior structures,
(2) evaluate or calculate internal processes in semiconductor or anisotropic materials, devices or wafers,
(3) test integrated circuits, devices, materials or electromagnetic signals that act upon or within the semiconductor or anisotropic materials, wafers, devices or processes,
(4) determine or calculate the effects of stresses, energies or signals acting upon at least one of the following: the semiconductor or anisotropic materials, dielectric materials, conductors, and within materials adjacent to, the feature, devices and wafers,
(5) determine or calculate at least one effect of energies or signals acting upon or within the semiconductor or anisotropic materials, dielectric materials, conductors, and within materials adjacent to, devices, features, or wafers,
(6) monitor, evaluate, calculate or determine the effectiveness or efficiency of the processes or materials to create semiconductor or anisotropic materials, devices, features, wafers or interior structures, or
(7) determine or calculate the effects of changes to process, configuration, or materials and identify or calculate at least one change that affects the semiconductor or anisotropic materials, devices, features, wafers or interior structures.

20. A method for optical interferometric testing and displaying internal stresses of at least one of the following: a semiconductor or anisotropic material, a semiconductor or anisotropic device, a wafer while being developed and evaluated or manufactured, or displaying the effects of signals acting upon the device or wafer under test being comprised of a semiconductor or anisotropic material having an exterior surface and interior structures, or feature, using a holographic optical interference system with at least one light source providing at least one light beam of coherent wavelength with a wavelength to which the semiconductor or anisotropic material is at least semi-transparent or transparent, the method comprising, imposing the object beam on the exterior surface of the semiconductor or anisotropic material to generate a transmitted object beam through the interior structures of the semiconductor or anisotropic material and interior surfaces of the semiconductor or anisotropic material to generate a transmitted beam passing through the interior surfaces of the semiconductor or anisotropic material or feature, adjusting the angle or optical pathway length of a reference beam relative to an object beam between a plurality of angles with the semiconductor or anisotropic material or device being in at least one state for each angle of the reference beam, or adjusting said attributes of the object beam relative to the reference beam, imposing the transmitted object beam and the reference beam onto one or more detection devices to create or record a plurality of interference or interferometric patterns of the transmitted object beam with the reference beam, one at each of the plurality of angles of the reference beam, comparing the plurality of live or recorded interference or interferometric patterns to one another to determine or calculate at least one characteristic within the semiconductor or anisotropic material or feature, using the plurality of interference or interferometric patterns of one or of differing infrared or thermal wavelengths to perform at least one of the following:
(1) test, shape, calculate or determine the semiconductor or anisotropic materials, devices, feature, wafers or interior structures,
(2) evaluate at least one internal process in at least one of the following: the semiconductor or anisotropic material, device, feature, or wafer,
(3) test at least one of the following: an integrated circuit, a device, a material, an electromagnetic signal acting upon or within the semiconductor or anisotropic material, wafer, device, the effects of processes upon such,
(4) determine or calculate the effects of such energies or stresses or signals acting upon or within at least one of the following: the semiconductor or anisotropic material, dielectric materials, conductors, and within materials adjacent to, the feature, device or wafer,
(5) determine or calculate at least one effect of energies or signals acting upon or within the semiconductor or anisotropic materials, dielectric materials, conductors, and within materials adjacent to, devices, features, or wafers
(6) monitor, evaluate, calculate or determine the effectiveness or efficiency of the processes or materials to create semiconductor or anisotropic materials, devices, features, wafers or interior structures, or
(7) determine or calculate the effects of changes to process, configuration, or materials and identify or calculate at least one change that affects the semiconductor or anisotropic materials, devices, features, wafers or interior structures.

* * * * *